United States Patent [19]

Atwater

[11] 4,401,624

[45] Aug. 30, 1983

[54] BUFFERED SOLUTIONS WHICH HAVE A REDUCED CORROSIVE NATURE

[76] Inventor: Charles B. Atwater, 3401 Hillview Ave., P.O. Box 10850, Palo Alto, Calif. 94303

[21] Appl. No.: 355,493

[22] Filed: Mar. 8, 1982

[51] Int. Cl.[3] .......................... A21D 2/14; A23B 4/12; C23F 11/12

[52] U.S. Cl. ................................ 422/12; 252/389 R; 252/396; 422/17; 424/317; 426/25; 426/321; 426/331; 426/653; 426/654; 426/807; 562/606; 562/607

[58] Field of Search ............ 252/389 R, 396; 422/12, 422/17; 424/317; 426/321, 331, 25, 653, 654, 426/807; 562/606, 607

[56] References Cited

U.S. PATENT DOCUMENTS

| | | | |
|---|---|---|---|
| 2,898,372 | 8/1959 | Anderson | 426/653 |
| 3,008,986 | 11/1961 | Hyson | 562/606 |
| 3,836,655 | 9/1974 | Kensler et al. | 424/286 |
| 4,016,294 | 4/1977 | Globe et al. | 426/331 |
| 4,112,122 | 9/1978 | Long | 426/335 |
| 4,199,606 | 4/1980 | Bland | 426/335 |

Primary Examiner—Irwin Gluck

[57] ABSTRACT

A method is disclosed for preparing and using buffered aqueous solutions of carboxylic acids and metal salts of carboxylic acids. Such solutions are useful as mold inhibitors in bread, cakes, and animal feeds. Buffered aqueous solutions of about 40 to 80 percent of compounds of carboxylic acids and carboxylic acid metal salts, such as sodium diacetate, sodium dipropionate, sodium dibutyrate or sodium dibenzoate have been found to have a reduced corrosive nature to metals and alloys used to contain, transport, and apply these solutions, thereby permitting the use of these metals and alloys in existing and new facilities.

5 Claims, No Drawings

4,401,624

BUFFERED SOLUTIONS WHICH HAVE A REDUCED CORROSIVE NATURE

BACKGROUND OF THE INVENTION

1. Field of the Invention

The present invention relates to improvements in the manufacture, handling and use of aqueous carboxylic acids by the formation of a buffered solution of a carboxylic acid and a carboxylic acid metal salt. Such aqueous solutions can be used in the preservation of raw or processed agricultural crop products, byproducts and derivatives thereof, particularly animal feeds and cereals which are subject to microbiological degradation and mold formation. The aqueous solutions of the present invention may be used with a large number of metal containers, piping, etc. wherein reduced corrosion of the metal is desired.

2. Related Disclosures

It has long been known that some carboxylic acids, such as acetic acid, propionic acid and butyric acid either alone, mixed, in solution or on a carrier material may be useful as a preservative for foodstuffs. For example see U.S. Pat. Nos. 2,154,449; 3,812,269; 3,836,655; and 4,199,606; all of which are incorporated herein by reference.

The preparation and use of sodium or potassium acetates, propionates and butyrates are also useful as mold inhibitors and are used in animal husbandry as described in U.S. Pat. Nos. 2,895,990; 2,898,372; and 4,112,122; which are also incorporated herein by reference.

The use of an odor-controlled sodium propionate-sodium dipropionate composition for use in the baking industry to prevent mold development in foodstuffs is described in U.S. Pat. No. 3,008,986, which is incorporated herein by reference. Sodium dipropionate, as used herein, is a compound of definite chemical composition having the following formula:

$$CH_3CH_2C(O)O^- {}^+Na.CH_3CH_2C(O)OH$$

It has long been known that aqueous solutions of carboxylic acids, and metal salts of carboxylic acids are corrosive to many types of metals and metal alloys used to contain, transport or apply these compositions. To solve these problems, some users have resorted to plastic containers, coated metal containers and piping, or to very expensive alloys. The discovery of a new, useful and more efficient solution which has a reduced corrosive nature to these metals is thus to be desired.

An object of this invention is the preparation of a buffered aqueous solution of a carboxylic acid metal-carboxylic acid compound useful for preservation of foodstuffs and animal foods. It is a further object of this invention to use such aqueous solutions which have a reduced corrosive nature to the metals, alloys, etc. employed in its transportation, storage and application. Other objects of the invention will appear hereinafter.

SUMMARY OF THE INVENTION

One aspect of the present invention is the discovery that certain aqueous solutions of compounds formed of a carboxylic acid metal salt and a carboxylic acid are buffers which have reduced corrosive nature to the metals used to contain and transport these solutions.

More specifically, the invention relates to a method of reducing metal corrosion by use of a liquid chemical composition comprising an aqueous solution of a carboxylic acid and a metal salt of a carboxylic acid wherein a compound is present which is comprised of (a) about one equivalent of a metal salt of a carboxylic acid having the formula $R'C(O)O^- {}^+M$;
(b) about one equivalent of a carboxylic acid having the formula $R''C(O)OH$; and
(c) water to produce an aqueous solution containing about 40 to about 80 percent by weight of a compound of the formula:

$$R'C(O)O^- {}^+M.R''C(O)OH$$

wherein:

R' and R" are independently selected from the group consisting of methyl, ethyl, propyl, iso-propyl, butyl, iso-butyl, tert-butyl and benzyl; and M is selected from the group consisting of sodium, potassium and calcium.

DETAILED DESCRIPTION OF THE INVENTION

The general equation for the buffered reaction (equilibrium) in water is shown below:

$$R'C(O)O^- {}^+M.R''C(O)OH \xrightleftharpoons{H_2O}$$

$$R'C(O)O^- {}^+M + R''C(O)OH \xrightleftharpoons{H_2O} R'C(O)O^- + {}^+M +$$

$$R''C(O)O^- + H^+$$

For the purposes of this invention the compound, $R'C(O)O^- {}^+M.R''C(O)OH$, in an aqueous solution may also include large quantities of dissociated species (e.g., $R'C(O)O^-$, ${}^+M$, $R''C(O)O^-$, $H^+$, $R''C(O)O^- {}^+M$, $R''C(O)OH$ shown in the above equation).

As can be seen from the preparation described in a subsequent example, the buffered aqueous solutions can range from about 40 to 80 percent in concentration of the carboxylic acid metal salt in combination with the carboxylic acid. The pH of the solution is usually between the values of 5 and 7. A presently more preferred concentration range of the compound is about 65 to 75 percent by weight. A presently most preferred concentration of the compound is about 70 percent by weight.

The metal portion of the salt (M), for this invention, may be selected from the group consisting of sodium, potassium, and calcium. A presently most preferred metal is sodium.

The carboxylic acid portion of the carboxylic acid metal salt may be selected from the group consisting of carboxylic acids, acetic, propionic, butyric, iso-butyric, valeric, iso-valeric and benzoic acid. A presently preferred group of acids is the linear alkyl carboxylic acids. A presently most preferred carboxylic acid is propionic acid, where R' is ethyl.

The free carboxylic acid may be independently selected from the group consisting of acetic, propionic, butyric, iso-butyric, valeric, iso-valeric, and benzoic acids. The presently most preferred carboxylic acid is propionic acid, where R" is ethyl.

The presently most preferred embodiment of this invention is about a 70 percent by weight of sodium dipropionate having the formula, $CH_3CH_2C(O)O^- {}^+Na.CH_3CH_2C(O)OH$ in an aqueous solution. Also within the scope of this invention is the compound R'C(O)O—M—OC(O)R" where M is calcium ($Ca^{+2}$), that is R'C(O)O—Ca—OC(O)R", where R' and R" are as defined herein.

The compounds useful in this invention can be made combining about one equivalent of $R'C(O)O^-+M$ and about one equivalent of R"C(O)OH in an appropriate amount of water. For instance, when about 70 g of crystalline sodium dipropionate, $CH_3CH_2C(O)O^-+M \cdot CH_3CH_2C(O)OH$, is dissolved in about 30 g of water, a 70 percent solution by weight of dissociated sodium dipropionate is obtained.

The compounds may also be prepared by treating the carboxylic acid with a metal hydroxide either as a solid or in aqueous solution and then diluting to the desired final concentration.

Many metals and alloys will exhibit reduced corrosion in the presence of the liquid chemical of this invention. These metals include:

| American Society of Mechanicl Engineers (ASME) | |
|---|---|
| Grade A-36 | Black Iron |
| Grade A-285C | Steel |
| Grade A 515-70 | Steel |
| Grade A 516-70 | Steel |
| Grade A 517-70 | Steel |
| American Society for Testing Materials (ASTM) | |
| A-106 Grade A | Steel |
| A-106 Grade B | Steel |
| A-53 Grade A | Steel |
| A-53 Grade B | Steel |
| A-307 Grade B | Steel |
| American Standards Association (ASA) | |
| B-16.4 | Steel |
| B-16.3 | Steel |
| B-16.5 | Steel |

For example, black iron (i.e., ASME A-36 Grade Steel) of the type used in containers and piping at many industrial and agricultural locations has been shown to have reduced corrosion when in contact with the liquid chemical of this invention.

To be useful in industrial and agricultural applications these solutions should have a freezing point below 10° C., otherwise, the piping and equipment may become clogged. It has been found that the aqueous solutions of this invention having from 40 to 80 percent by weight in concentration have freezing temperature of 10° C. or less. An aqueous solution of 70 percent by weight of $CH_3CH_2C(O)O^-+M \cdot CH_3CH_2C(O)OH$ has a freezing point below 0° C., where M is sodium.

DESCRIPTION OF SPECIFIC EMBODIMENTS

The following description is given to enable those skilled in this art to more clearly understand and practice the present invention. It should not be considered as a limitation upon the scope of the invention but merely as being illustrative and representative thereof.

PREPARATION 1

About 70 g of crystalline sodium dipropionate is dissolved in 30 g of water to yield a 70 percent solution by weight of dissociated sodium dipropionate.

PREPARATION 2

About 39.53 g of sodium propionate and 30.47 g of propionic acid are mixed with 30 g of water to produce a 70 percent solution by weight of dissociated sodium dipropionate.

The resulting buffered solution contains about 39.53 percent of sodium propionate, 30.47 percent of propionic acid and 30 percent water.

PREPARATION 3

To about 60.94 g of propionic acid in 6.12 g of water is slowly added 32.94 g of a 50% solution of sodium hydroxide. The resulting buffered solution contains 60.94% as propionic acid or 70% dissociated sodium dipropionate and has a pH value of 6.5±0.5.

PREPARATION 4

About 80 g of crystalline sodium dipropionate is dissolved in 20 g of water to yield an 80 percent solution by weight of dissociated sodium dipropionate.

PREPARATION 5

About 40 g of crystalline sodium dipropionate is dissolved in 60 g of water to yield a 40 percent solution by weight of dissociated sodium dipropionate.

PREPARATION 6

About 80 g of crystalline potassium dipropionate is dissolved in 20 g of water to yield an 80 percent solution by weight of dissociated potassium dipropionate.

PREPARATION 7

About 40 g of crystalline potassium dipropionate is dissolved in 60 g of water to yield a 40 percent solution by weight of dissociated potassium dipropionate.

PREPARATION 8

About 70 g of mixed, crystalline salt sodium acetate-propionic acid is dissolved in 30 g of water to yield a 70 percent solution by weight of dissociated sodium acetate and propionic acid.

PREPARATION 9

About 70 g of calcium propionate-propionic acid is dissolved in 30 g of water to yield a 70 percent solution by weight of dissociated calcium propionate and propionic acid.

EXAMPLE 1

Weighed strips of metal of the same dimensions (1 inch by 4 inches) each weighing about 31 g were submerged in water, aqueous propionic acid and aqueous sodium dipropionate solution in tightly closed glass bottles. At the beginning of the study the concentration of propionic acid was 61 percent by weight and the sodium dipropionate solution contained an equivalent of 61 percent by weight as propionic acid by assay.

The strips were periodically removed, cleaned, dried, and weighed to determine weight losses, if any. Duplicate determinations, for each type of metal and for each of the test solutions were made as well as duplicate controls for each metal in double distilled water. All tests were conducted at ambient temperature.

As is seen in Table 1 below, carbon steel (ASME—Grade A36) is significantly less corroded by after two months a 70% solution of aqueous sodium dipropionate, than by a 61 percent aqueous solution of propionic acid.

TABLE 1

CORROSION DATA

| Material | % Weight Loss of Metal After Two Months | | |
|---|---|---|---|
| | Distilled Water | 70% Aqueous Sodium Dipropionate | 61% Aqueous Propionic Acid |
| Carbon Steel | 0.6 | 0.01 | 6.1 |
| No. 304 Stainless Steel | <0.01 | <0.01 | <0.01 |
| No. 316 Stainless Steel | <0.01 | <0.01 | <0.01 |

EXAMPLE 2

As is seen in Table 2 below, carbon steel (ASME—Grade A36) from Example 1 is significantly less corroded after a total of six months of testing using a 70% solution of aqueous sodium dipropionate, than by a 61% aqueous solution of propionic acid.

TABLE 2

CORROSION DATA

| Material | % Weight Loss of Metal After Six Months | | |
|---|---|---|---|
| | Distilled Water | 70% Aqueous Sodium Dipropionate | 61% Aqueous Propionic Acid |
| Carbon Steel | 1.7 | 0.01 | 40. |
| No. 304 Stainless Steel | <0.01 | <0.01 | <0.01 |
| No. 316 Stainless Steel | <0.01 | <0.01 | <0.01 |

EXAMPLE 3

The crystallization temperature for sodium dipropionate in solution needs to be below ambient temperature so that the aqueous buffered solution can be used in metal piping over a wide temperature range. The results of sodium dipropionate concentration in water versus temperature experiments are summarized in Table 3.

TABLE 3

Aqueous Sodium Dipropionate Concentration and Crystallization Temperature

| Sodium Dipropionate (Weight Percent) | Crystallization Temperature (°C.) |
|---|---|
| 70 | −5 |
| 65 | −3 |
| 60 | <−30 |
| 55 | <−30 |
| 50 | <−30 |

While the present invention has been described with reference to specific embodiments thereof, it should be understood by those skilled in this art that various changes may be made and equivalents may be substituted without departing from the true spirit and scope of the invention. In addition, many modifications may be made to adopt a particular situation material, or composition of matter, process, process step, or steps or the present objections of this invention without departing from its essential teachings.

What is claimed is:

1. A method for reducing the corrosion of metals in contact with an aqueous solution of a carboxylic acid which comprises maintaining said metal in contact with an aqueous solution of:
    (a) about one equivalent of a metal salt of a carboxylic acid having the formula R'C(O)O$^-$ $^+$M;
    (b) about one equivalent of a carboxylic acid having the formula R''C(O)OH; and
    (c) water to produce an aqueous solution containing about 40 to about 80 percent by weight of a compound having the formula R'C(O)O$^-$ $^+$M.R''C(O)OH wherein:
   R' and R'' are independently selected from the group consisting of methyl, ethyl, propyl, iso-propyl, butyl, iso-butyl, tert-butyl and benzyl; and
   M is selected from the group consisting of sodium, potassium, and calcium.

2. The method of claim 1 wherein said solution contains about 65 to about 75 percent by weight of said compound.

3. The method of claim 1 wherein R' and R'' are ethyl and M is sodium.

4. The method of claim 1 wherein said solution contains about 70 percent by weight of said compound.

5. The method of claim 1 wherein said solution contains about 70 percent by weight of said compound, R' and R'' are ethyl, and M is sodium.

* * * * *

Disclaimer 4,401,624.—*Charles B. Atwater*, Springfield, Mo. BUFFERED SOLUTIONS WHICH HAVE A REDUCED CORROSIVE NATURE. Patent dated Aug. 30, 1983. Disclaimer filed Dec. 20, 1984, by the assignee, *Syntex (U.S.A.) Inc.*

Hereby enters this disclaimer to all claims of said patent.
[*Official Gazette June 4, 1985.*]

REEXAMINATION CERTIFICATE (426th)
United States Patent [19]
Atwater

[11] B1 4,401,624
[45] Certificate Issued Nov. 26, 1985

[54] BUFFERED SOLUTIONS WHICH HAVE A REDUCED CORROSIVE NATURE

[75] Inventor: Charles B. Atwater, Palo Alto, Calif.

[73] Assignee: Syntex Inc., Palo Alto, Calif.

Reexamination Request:
No. 90/000,627, Sep. 13, 1984

Reexamination Certificate for:
Patent No.: 4,401,624
Issued: Aug. 30, 1983
Appl. No.: 355,493
Filed: Mar. 8, 1982

Disclaimer of claim(s) 1-5
Filed Dec. 20, 1984 (1055 P.G. 4)

[51] Int. Cl.$^4$ .................. A21D 2/14; A23B 4/12; C23F 11/12
[52] U.S. Cl. .................. 422/12; 252/389 R; 252/396; 422/17; 426/25; 426/321; 426/331; 426/653; 426/654; 426/807; 514/557; 514/568; 562/606; 562/607

[56] References Cited

U.S. PATENT DOCUMENTS

| | | | |
|---|---|---|---|
| 2,898,372 | 8/1959 | Anderson | 426/653 |
| 3,008,986 | 11/1961 | Hyson | 562/606 |
| 3,836,655 | 9/1974 | Kensler et al. | 424/286 |
| 4,016,294 | 4/1977 | Glabe et al. | 426/331 |
| 4,112,122 | 9/1978 | Long | 426/335 |
| 4,179,522 | 12/1979 | Huitson | |
| 4,199,606 | 4/1980 | Bland | 426/335 |

OTHER PUBLICATIONS

Declaration of Dr. David Berry executed Feb. 22, 1978 and filed May 30, 1978 in the file of U.S. patent application Ser. No. 735,160, filed Oct. 26, 1976, which matured into U.S. Pat. No. 4,179,522, issued Dec. 18, 1979, to John J. Huitson.

*Primary Examiner*—John F. Terapane
*Assistant Examiner*—Mathew A. Thexton

[57] ABSTRACT

A method is disclosed for preparing and using buffered aqueous solutions of carboxylic acids and metal salts of carboxylic acids. Such solutions are useful as mold inhibitors in bread, cakes, and animal feeds. Buffered aqueous solutions of about 40 to 80 percent of compounds of carboxylic acids and carboxylic acid metal salts, such as sodium diacetate, sodium dipropionate, sodium dibutyrate or sodium dibenzoate have been found to have a reduced corrosive nature to metals and alloys used to contain, transport, and apply these solutions, thereby permitting the use of these metals and alloys in existing and new facilities.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-5 are now disclaimed.

* * * * *